United States Patent [19]

Carter et al.

[11] 4,100,136
[45] Jul. 11, 1978

[54] FLUOROCARBON SILOXANE COMPOSITIONS

[75] Inventors: Philip L. Carter; Yung K. Kim; Michael O. Riley, all of Midland, Mich.

[73] Assignee: Dow Corning Corporation, Midland, Mich.

[21] Appl. No.: 803,110

[22] Filed: Jun. 3, 1977

Related U.S. Application Data

[62] Division of Ser. No. 647,473, Jan. 8, 1976, Pat. No. 4,057,566.

[51] Int. Cl.² .............................................. C08G 77/04
[52] U.S. Cl. .................................. 528/11; 260/37 SB; 260/825; 264/102
[58] Field of Search .......... 260/46.5 UA, 825, 46.5 G, 260/37 SB, 46.5 H

[56] References Cited

U.S. PATENT DOCUMENTS

| | | | |
|---|---|---|---|
| 3,344,160 | 9/1967 | Holbrook | 260/46.5 |
| 3,542,830 | 11/1970 | Kim et al. | 260/448.2 |
| 3,647,740 | 3/1972 | Loree et al. | 260/46.5 UA |
| 3,975,362 | 8/1976 | Kim et al. | 260/46.5 UA |
| 3,989,667 | 11/1976 | Lee et al. | 260/46.5 UA |
| 4,057,566 | 11/1977 | Carter et al. | 260/37 SB |

*Primary Examiner*—Melvyn I. Marquis
*Attorney, Agent, or Firm*—George A. Grindahl

[57] ABSTRACT

Fluorocarbon siloxanes of the formula

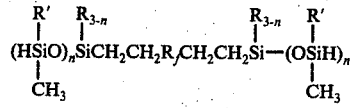

are disclosed. Their use as reversion resistant curing agents in curable compositions comprising reversion resistant siloxanes of the formula

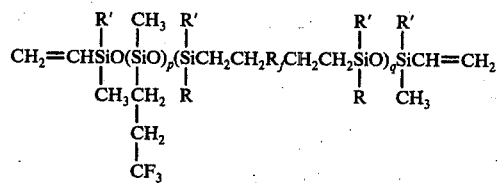

are also disclosed.

14 Claims, No Drawings

FLUOROCARBON SILOXANE COMPOSITIONS

This is a division of application Ser. No. 647,473, filed Jan. 8, 1976 now U.S. Pat. No. 4,057,566.

BACKGROUND OF THE INVENTION

1. Field of the Invention

This invention relates to new fluorocarbon siloxanes and to their use as curing agents in fluorocarbon silicone compositions.

2. Description of the Prior Art

New fluorocarbon silanes, siloxanes, and silicone compositions have been described by Kim, et al. in U.S. Pat. No. 3,542,830 and by Loree et al., in U.S. Pat. No. 3,647,740. The cured silicone compositions of Loree, et al. display increased resistance to the loss of elastomeric properties under confined conditions at elevated temperatures, a phenomenon known as reversion. In the extreme, this loss of elastomeric properties can result in the conversion of an elastomer to a soupy liquid. While the cured compositions of Loree, et al., have better reversion resistance than cured compositions based on poly(methyl-3,3,3-trifluoropropylsiloxane), the low temperature flexibility of the former do not equal that of the latter.

New fluorocarbon siloxanes and silicone compositions have been described by Yung K. Kim and Michael O. Riley in U.S. Application Ser. No. 572,583 of Apr. 28, 1975, entitled, "Low Temperature Reversion Resistant Organosilicon Polymers" now U.S. Pat. No. 3,975,362 and assigned to the assignee of this application which, in the cured state, display reversion resistance and improved low temperature flexibility.

The compositions of Loree, et al. and the compositions of Kim and Riley are curable with several curing agents including the crosslinking agents that are described by Holbrook in U.S. Pat. No. 3,344,160. However, in some instances, the reversion resistance of these new fluorocarbon siloxanes and silicone compositions is limited by the particular curing agent that is used to cure the composition. In particular, when certain compositions of Loree, et al., that contain silicon-bonded vinyl groups are cured with the crosslinking agents of Holbrook that contain silicon-bonded hydrogen atoms, reversion resistant is limited.

SUMMARY OF THE INVENTION

It is an object of this invention to provide new fluorocarbon siloxanes.

Another object of this invention is to provide new fluorocarbon siloxanes having silicon-bonded hydrogen atoms that are useful for curing fluorocarbon siloxanes of the art having silicon-bonded vinyl radicals.

It is a further object of this invention to provide curable fluorocarbon silicone compositions that have improved reversion resistance in the cured state.

These and other objects are realized via the fluorocarbon siloxanes of this invention comprising at least two silicon-bonded H(CH₃)R'SiO units that are joined by a divalent fluorocarbon group having the formula —CH₂CH₂R$_f$CH₂CH₂—.

DESCRIPTION OF THE INVENTION

This invention relates to a composition of the formula

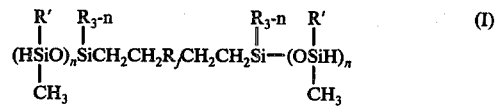

wherein each R and R' is independently methyl, phenyl or 3,3,3-trifluoropropyl; R$_f$ is a perfluoroalkylene radical of 2 to 10 carbon atoms, a perfluorocycloalkylene radical, or a perfluoroalkylene radical of 2 to 10 carbon atoms or a perfluorocycloalkylene radical containing one or more —C—O—C— linkages; and each $n$ is independently 1, 2 or 3.

The compositions of this invention (I) can be prepared by any suitable method for the preparation of siloxanes containing silicon-bonded hydrogen atoms. Preferably said compositions are prepared from fluorocarbon silanes of the formula

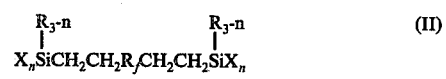

where X is hydroxy or a hydrolyzable radical, such as chloro, each $n$ is, independently, 1, 2, or 3 and R and R$_f$ are as defined above. The preparation of said fluorocarbon silanes (II) is described by Kim, et al. in U.S. Pat. No. 3,542,830 which is hereby incorporated by reference to show the preparation of fluorocarbon silanes and the types of hydrolyzable radicals, X, that can be included in the fluorocarbon silane.

In the preferred method for the preparation of the compositions of this invention (I) the fluorocarbon silane (II) wherein X is chloro is cohydrolyzed with an excess of an appropriate chlorohydrosilane, such as H(CH₃)₂SiCl or H(CH₃)(C₆H₅)SiCl or H(CH₃)—(CF₃CH₂CH₂)SiCl or a mixture of two or more of said chlorohydrosilanes and the resulting fluorocarbon siloxane (I) is isolated by distillation. In those cases where the resulting fluorocarbon siloxane has a sufficiently low boiling point it can be purified by fractional distillation. In other instances purification of (I) can be accomplished by distilling the more volatile by-produced disiloxanes such as H(CH₃)₂Si-OSi(CH₃)₂H, leaving the fluorocarbon siloxanes of this invention in the undistilled form. In an undistilled form, fluorocarbon siloxane (I) may be essentially pure. In some cases, however; for example, when a sufficient excess of the appropriate chlorohydrosilane was not used in the cohydrolysis reaction with fluorocarbon silane (II), there may be present, in undistilled (I), small quantities of higher-molecular-weight fluorocarbon siloxanes which bear silicon-bonded H(CH₃)R'SiO radicals. These higher-molecular-weight fluorocarbon siloxanes are not detrimental to the efficacy of the compositions of this invention (I) as curing agents for the curable compositions of this invention, hereinafter described.

An excess of an appropriate chlorohydrosilane such as H(CH₃)₂SiCl is used to assure that a maximum number of silicon-bonded chlorine atoms in the fluorocarbon silane are replaced with H(CH₃)R'SiO— radicals such as H(CH₃)₂SiO—. It is necessary to cohydrolyze at least 1 mole, preferably at least 2 moles, of chlorohydrosilane with every mole of silicon-bonded chlorine atoms in the fluorocarbon silane (II). For example, it is necessary that at least 4, and preferably 8, moles of H(CH₃)₂SiCl be cohydrolyzed with every mole of $Cl_2(CH_3)SiCH_2CH_2CF_2CF_2CH_2CH_2Si(CH_3)Cl_2$ to assure a high yield of the desired

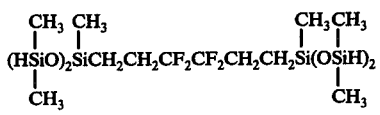

Greater excesses of the chlorohydrosilane will assure higher yields of (II).

The fluorocarbon siloxanes (I) of this invention may also be prepared by allowing (II) to react with other compounds that will replace the X radical with the desired $H(CH_3)R'SiO-$ radical. Said compounds are well known in the organosilicon art and include disiloxanes such as $\{H(CH_3)R'Si\}_2O$, such as $\{H(CH_3)_2Si\}_2O$; silazanes such as $\{H(CH_3)R'Si\}_2NH$, such as $\{H(CH_3)(C_6H_5)Si\}_2NH$; acyloxy silanes such as $H(CH_3)R'SiO_2CCH_3$, such as $H(CH_3)(CF_3CH_2CH_2)SiO_2CCH_3$; alkoxy silanes such as $H(CH_3)R'SiOMe$, aminosilanes such as $H(CH_3)R'SiNH_2$, ketoximosilanes such as $H(CH_3)R'SiON=C(CH_3)_2$, amidosilanes such as $H(CH_3)R'SiN-(CH_3)COCH_3$ and the like. One skilled in the art will, with little experimentation, determine the optimum conditions that are needed to produce (I) from (II) in high yield using said compounds.

In the compositions of this invention (I), $R_f$ can be a perfluoroalkylene radical of from 2 to 10 carbon atoms such as

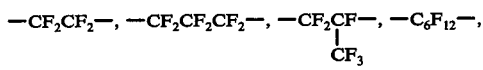

a perfluorocycloalkylene radical such as

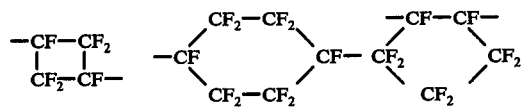

or a perfluoroalkylene radical of 2 to 10 carbon atoms or a perfluorocycloalkylene radical containing one or more —C—O—C— linkages such as

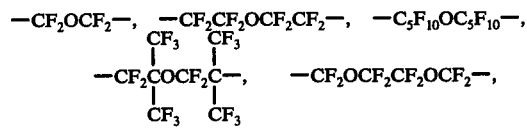

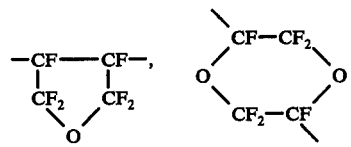

Fluorocarbon siloxanes (I) in which $R_f$ has from 2 to 6 carbon atoms are preferred because they possess boiling points sufficiently low to permit their purification by fractional distillation. Fluorocarbon siloxanes (I) wherein $R_f$ is $-CF_2CF_2-$ are most easily prepared and are highly preferred.

In the compositions of this invention (I) each R and R' is independently methyl, phenyl, or 3,3,3-trifluoropropyl. It is to be understood that all R and R' can be identical or there can be two or more different R and R' in fluorocarbon siloxane (I). Preferably R' is methyl.

Furthermore, each n can have independently, a value of 1, 2, or 3.

For example, in the highly preferred fluorocarbon siloxanes (I) wherein R' is methyl and $R_f$ is $-CF_2CF_2-$, there is obtained, when each n is equal to 1, a dihydrogen fluorocarbon siloxane of the formula

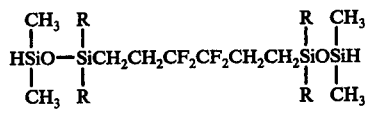

wherein each R is independently methyl, phenyl or 3,3,3-trifluoropropyl. In the above example, when each n is 2 there is obtained a tetrahydrogen fluorocarbon siloxane of the formula

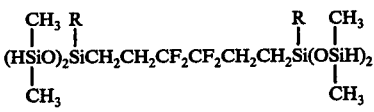

A tetrahydrogen fluorocarbon siloxane (I) is also obtained when one n has a value of 3 and the other n has a value of 1. In a similar fashion there is obtained, trihydrogen fluorocarbon siloxanes when the sum of both n is equal to 3, pentahydrogen fluorocarbon siloxanes when the sum of both n is equal to 5 and hexahydrogen fluorocarbon siloxanes when the sum of both n is equal to 6. Fluorocarbon siloxanes (I) wherein each n has the same value are preferred because of the relative ease of preparation of the precursor fluorocarbon silane (II).

The fluorocarbon siloxane compositions (I) of this invention are useful as curing agents in vinyl-containing polyorganosiloxane compositions containing silicon-bonded fluorinated hydrocarbon radicals, such as are hereinafter described.

Additionally, this invention relates to a curable composition consisting essentially of a homogeneous mixture of (A) a random or an alternating siloxane of the formula

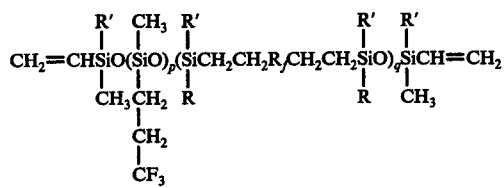

(B) a curing agent of the formula

and (C) an effective amount of a platinum-containing catalyst; where, in (A) and (B), each R and R' is independently methyl, phenyl or 3,3,3-trifluoropropyl, each $R_f$ is independently a perfluoroalkylene radical of 2 to 10 carbon atoms, a perfluorocycloalkylene radical, or a perfluoroalkylene radical of 2 to 10 carbon atoms or a perfluorocycloalkylene radical containing one or more —C—O—C— linkages; p has a value of from 0 to 2q inclusive, and when p has a value greater than q, siloxane (A) is only an alternating copolymer having no more than 2 adjacent $CH_3(CF_3CH_2CH_2)SiO$ units, $q$ has an average value of at least 5, each $n$ is independently 1, 2, or 3, there being an average of greater than 2.0 silicon-bonded hydrogen atoms per molecule of (B) and the amount of (B) being such that there is, in said curable composition, from 0.5 to 3.0 silicon-bonded hydrogen atoms for every silicon-bonded vinyl radical.

In the curable compositions of this invention the siloxane (A) can be any of the siloxane polymers or copolymers described by Loree, et al., in U.S. Pat. No. 3,647,740 or any of the alternating copolymers described by Kim and Riley in U.S. Application Ser. No. 572,583, now U.S. Pat. No. 3,975,362 hereinbefore noted, as long as they are described by the formula for (A). Said Loree, et al. patent and said Kim and Riley application are hereby fully incorporated by reference to show the preparation of siloxane (A). It should be noted that the arrangement of $p$ units and $q$ units in the formula for (A) is a matter of descriptive convenience only and should not be construed as necessarily indicating any particular arrangement of said units in (A). Particular arrangements of said units are shown in (III), (IV), and (V), depending on the value of $p$.

When $p$ is equal to zero siloxane (A) is a siloxane polymer of the formula

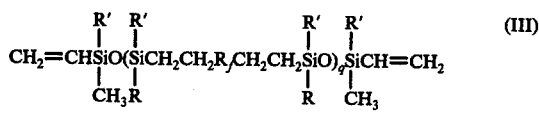

When $p$ has a value of from greater than zero to $q$, inclusive, siloxane (A) can be either a random copolymer of the formula

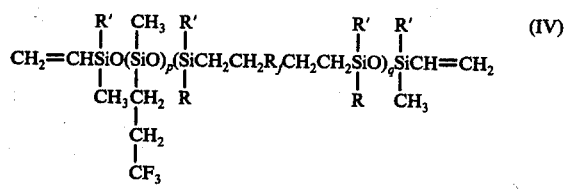

or an alternating copolymer of the formula

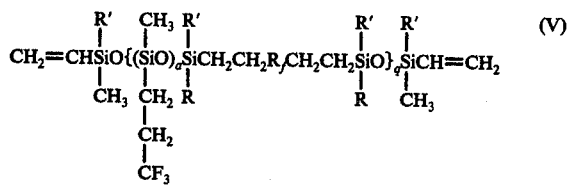

wherein $a$ is 0, 1 or 2 and the average value of $a$ is from greater than zero to 1, inclusive.

A random copolymer, for the purposes of this invention, is a copolymeric polysiloxane that is obtained by a method of preparation in which there is no attempt to arrange the siloxane units of said polysiloxane, except endblocking siloxane units, in any specific order.

When $p$ has a value of from greater than $q$ to $2q$, inclusive, siloxane (A) must be an alternating copolymer of the formula (V) wherein $a$ is 0, 1 or 2 and the average value of $a$ is from greater than 1 to 2, inclusive.

Thus, when $p$ has a value equal to $q$, siloxane (A) can be either a random copolymer (IV) or an alternating copolymer (V) but when the value of $p$ exceeds the value of $q$, siloxane (A) must be an alternating copolymer (V), in order to maintain reversion resistance of the cured composition. Of course, siloxane (A) can also be any mixture of siloxanes (III) and/or (IV) and/or (V).

Each R and R' in (III), (IV), and (V) is independently, methyl, phenyl, or 3,3,3-trifluoropropyl and $R_f$ can be any of the $R_f$ radicals described for fluorocarbon siloxane (I) above. Preferably R' is methyl and $R_f$ has from 2 to 6 carbon atoms. Siloxanes (A) in which $R_f$ is $-CF_2CF_2-$ are most easily prepared and are highly preferred.

The curing agent (B) of the curable compositions of this invention can be any of the fluorocarbon siloxanes (I) of this invention as long as there is an average of greater than 2.0 silicon-bonded hydrogen atoms per molecule of (I). Thus, curing agent (B) can be any fluorocarbon siloxane of formula (I) wherein the sum of both $n$ is greater than 2, for example, 3, 4, 5, or 6. Curing agent (B) can also be any mixture of fluorocarbon siloxanes of the formula (I) wherein the average value for the sum of both $n$ is greater than 2.0, for example, 2.1, 2.4, 3, 3.5, 4, 4.2, 5, 5.8, or 6.

For example, curing agent (B) can be a fluorocarbon siloxane of the formula (I) wherein $R_f$ is $-CF_2CF_2-$, R' is $CH_3$, R is $CH_3$, one $n$ has a value of 2 and the other $n$ has a value of 1. Curing agent (B) can also be an equimolar mixture of a fluorocarbon siloxane (I) wherein $R_f$ is $-CF_2CF_2-$, R' is $CH_3$, R is $CH_3$ and each $n$ has a value of 2 and a fluorocarbon siloxane (I) wherein $R_f$ is $-CF_2CF_2-$, R' is $CH_3$, R is $CF_3CH_2CH_2$ and each $n$ has a value of 1. Furthermore, curing agent (B) can be a mixture of fluorocarbon siloxanes of formula (I) having identical R radicals, identical R' radicals, and identical $n$ values, but different $R_f$ radicals as long as the value of the sum of both $n$ values is greater than 2.0. Obviously, many other combinations of fluorocarbon siloxane (I) are suitable as curing agent (B) within the spirit and scope of this invention.

Platinum-containing catalyst (C) is any of the well-known platinum-containing materials that catalyze the addition reaction of silicon-bonded hydrogen atoms with silicon-bonded vinyl radicals. Preferred are the unsupported platinum-containing catalysts such as a solution of chloroplatinic acid in an organopolysiloxane as taught by Willing in U.S. Pat. No. 3,419,593 which is hereby incorporated by reference to show the preparation of a suitable platinum-containing catalyst (C). Other suitable platinum-containing catalyst include a solution of chloroplatinic acid in isopropyl alcohol and chloroplatinic acid catalysts described by Speier in U.S. Pat. No. 2,823,218. A particularly useful catalyst is a platinum-containing catalyst prepared according to Willing, supra, wherein the organopolysiloxane bears 3,3,3-trifluoropropyl radicals.

The amount of platinum-containing catalyst (C) to be used in the curable compositions of this invention is merely the amount that is effective to cure said compositions. An effective amount of (C) will depend upon the particular type of platinum-containing catalyst that is used and the conditions under which said compositions are cured. There should be sufficient (C) to provide at least one part by weight of platinum for every 1 million parts by weight of siloxane (A) in the curable compositions of this invention. Preferably there should be from 10 to 100 parts by weight of platinum per one million parts by weight of siloxane (A). Larger amounts of platinum are not detrimental but are unnecessary and costly.

The amount of curing agent (B) to be used in the curable compositions of this invention is narrowly restricted. There should be a sufficient amount of curing agent (B) in said curable composition so that there is from 0.5 to 3.0 silicon-bonded hydrogen atoms for every silicon-bonded vinyl radical in the composition. In addition to the silicon-bonded vinyl radicals of siloxane (A), there can be in the curable compositions of this invention, silicon-bonded vinyl radicals in the catalyst (C) and in other ingredients that are well-known components of curable silicone compositions, such as in treated fillers. All of the sources of silicon-bonded vinyl radicals in said composition must be considered when establishing an SiH/Si-vinyl ratio.

The curable compositions of this invention can contain other components that are common to the organosilicon rubber art such as reinforcing silica fillers such as fume silica, precipitated silica, silica aerogels; extending fillers such as diatomaceous earth, ground quartz, carbon black, asbestos and calcium carbonate; heat stability additives, oxidation inhibitors, pigments, platinum-catalyst inhibitors, adhesion promoters and the like as long as said components do not prevent the curing of said compositions.

The reinforcing silica fillers can be untreated or pretreated or treated in situ with the usual silica filler treating agents that are well known in the art. For compatibility with siloxane (A), the treated reinforcing silica fillers that are used in the compositions of this invention are best treated with said treating agents bearing silicon-bonded fluorine-containing radicals such as 3,3,3-trifluoropropyl radicals.

Platinum-catalyst inhibitors delay, but do not prevent, the curing of the curable compositions of this invention. Some inhibitors delay the curing of said compositions at room temperature for periods of weeks or months, but the compositions of this invention are all curable at elevated temperature, for example, about 70° C., but preferably above 100° C., in a short period of time, for example, one hour. Platinum-catalyst inhibitors which are suitable for the curable compositions of this invention include those described in U.S. Pat. Nos. 3,188,299; 3,188,300; 3,192,181; 3,344,111; 3,383,356; 3,445,420; 3,453,233; 3,453,234; 3,532,649, and those described by Lee and Marko in U.S. Application Ser. No. 528,966 of December 2, 1974 entitled, "Olefinic Siloxanes as Platinum Inhibitors" now U.S. Pat. No. 3,989,667 and assigned to the assignee of this invention.

The curable compositions of this invention are obtained whenever the siloxane (A), curing agent (B), and platinum-containing catalyst (C) are mixed, by any suitable method, in any order. A curing reaction will begin at room temperature as soon as (A), (B), and (C) are mixed. This curing reaction can be delayed by cooling said composition to a temperature below room temperature, for example, to −20° C. or lower. The curing reaction can also be delayed by admixing a platinum-catalyst inhibitor, hereinbefore described, to said curable compositions. Preferably any platinum catalyst inhibitor that is used is present when the catalyst (C) and the curing agent (B) are mixed.

The curable compositions of this invention can be prepared as a one-package composition or as a multi-package composition. For example, in a two-package composition, one package can contain siloxane (A), catalyst (C) and any fillers, pigments and additives and a second package can contain curing agent (B), any inhibitors, pigment, etc. The curable compositions of this invention are prepared when the several packages of a multi-package are mixed in the proper proportions.

The best way to prepare the curable compositions of this invention is to mix siloxane (A) and any fillers, in a polymer mixer or on a two-roll rubber compounding mill, using heat to facilitate thorough mixing and then add catalyst (C) and any pigments and additives to the cooled mixture of siloxane (A) and silica. To the mixture comprising siloxane (A) and catalyst (C), curing agent (B), and any inhibitor is then added to any suitable time.

The curable compositions of this invention will cure at room temperature but they are best cured by heating to about 100° C., for example, 150° C. Post curing of said compositions can be conducted, if desired, at temperatures as high as 200°–250° C. for periods of up to 24 hours.

The curable compositions of this invention have, in the cured state, improved reversion resistance at elevated temperatures compared to fluorocarbon siloxane compositions cured with prior art curing agents. The curable compositions of this invention are useful for the preparation of elastomeric materials such as sealants, encapsulants, molded parts, extruded parts, coatings and the like. The cured compositions of this invention are especially useful in environments of high temperature and hydrocarbon fuels and oils such as would be encountered in a high performance aircraft.

The following examples are illustrative only and should not be construed as limiting the invention which is properly delineated in the claims. All parts are parts by weight.

EXAMPLE 1

This example illustrates the preparation of the fluorocarbon silane (II) wherein R is $CH_3$—, $n = 2$, $x$ is chlorine and $R_f$ is —$CF_2CF_2$—.

A 500 ml. flask fitted with mechanical stirrer, reflux condenser, thermowell, and additional funnel was charged with 77.49 g. (0.5 mole) of $CH_2$=$CH(CF_2)_2CH$=$CH_2$ and 0.2 ml. of a 5% solution of chloroplatinic acid in isopropyl alcohol. The addition funnel was charged with 134.52 g. (1.2 mole) of $H(CH_3)SiCl_2$. Approximately one-half of the chlorosilane in the addition funnel was added with stirring to the flask over a period of 2 hours. The temperature was slowly raised to 70° C., at which point initiation of the reaction seemed to occur. The remaining $H(CH_3)SiCl_2$ was added and the mixture stirred overnight at 55° C. The resulting white solid was dissolved in dry toluene and stripped to remove low boiling impurities. The resulting product melted at 63° – 65° C.

IR, $H^1$ NMR and $F^{19}$ NMR spectroscopy and elemental analysis confirmed the following structure:

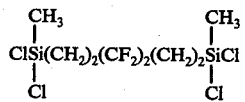

EXAMPLE 2

A 1-liter Morton flask fitted with a water-cooled condenser, addition funnel, and mechanical stirrer was charged with 179 ml. of water. The addition funnel was loaded with a solution of 40 g. (0.074 mole) of the fluorocarbon silane of Example 1, 55.7 g. (0.589 moles) of $H(CH_3)_2SiCl$ and 24 g. of toluene. The solution was added dropwise to the vigorously agitated water. At first, a solid precipitated. After approximately 1 hr. it was clear that an emulsion had formed. Toulene and water were added in an attempt to break the emulsion. This was followed by a number of washes with saturated sodium chloride solution. Finally the emulsion was filtered through a glass wool-packed Buchner funnel.

The organic layer was separated, washed to neutrality, and then dried over $CaSO_4$. Distillation on a spinning band column gave 18 g. (45%) of the fluorocarbon siloxane

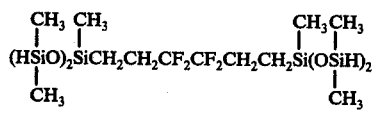

which had a boiling point of 148° C. at 0.25 mm. of Hg (33.3 pascal). Elemental analysis, nuclear magnetic resonance and infrared spectroscopy were consistant with the formula given.

EXAMPLE 3

A 3-liter flask fitted with condenser mechanical stirrer, and addition funnel was charged with 700 ml. of water, 100 ml. of toluene and 125 g. (1.5 mole) of $NaHCO_3$. The reactants, 65 g. (0.126 mole) of

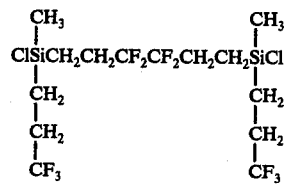

and 84.3 g. (0.77 mole) of $H(CH_3)_2SiCl$, were dissolved in approximately 200 ml. of toluene and the solution was transferred to the addition funnel. This chlorosilane mixture was added to the stirred water solution over the space of an hour and allowed to stir at room temperature for about 16 hours. The organic layer was then separated, washed with saturated NaCl solution, and dried. After filtering, the product was stripped of volatile material and distilled on a 36 inch (0.9 m) spinning band column.

Distillation yielded 64 g. of a clear liquid, which was 86% of the theoretical yield. IR, $H^1$ NMR and $F^{19}$ NMR spectroscopy and elemental analysis confirmed the following structure:

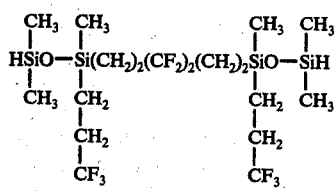

EXAMPLE 4

A first curable composition (i) was prepared by hand-mixing the following components and then further mixing them on a two-roll rubber compounding mill: 100 parts of a siloxane of the formula (III) wherein R' is $CH_3$—, R is $CF_3CH_2CH_2$—, $R_f$ is —$CF_2CF_2$— and $q$ has a value of about 17; 10 parts of a trimethylsiloxy-treated fume silica, 1 part of carbon black; a curing agent consisting of a mixture of 4.23 parts of the fluorocarbon siloxane of Example 2 and 5.68 parts of the fluorocarbon siloxane of Example 3; approximately 1.5 parts of a platinum-containing catalyst and 0.2 parts of methylbutynol. The resulting composition had a ratio of silicon-bonded hydrogen to silicon-bonded vinyl of 2.0, an average of approximately 2.9 silicon-bonded hydrogen atoms per molecule of curing agent and 75 ppm. platinum.

A second curable composition (ii) was prepared similarly except that the curing agent consisted of a mixture of 4.41 parts of the known $H(CH_3)_2SiO\{H(CH_3)_2SiO(CF_3CH_2CH_2)SiO\}_mSi(CH_3)_2H$ where $m$ had an average value of approximately 4, and 5.84 parts of the known $H(CH_3)_2SiO\{CH_3(CF_3CH_2CH_2)SiO\}_3Si(CH_3)_2H$. The resulting composition had a ratio of silicon-bonded hydrogen to silicon-bonded vinyl of approximately 2, an average of approximately 2.9 silicon-bonded hydrogen atoms per molecule of the curing agent and 75 ppm. platinum.

Both milled, curable compositions were deaired, placed in rectangular chases, deaired again and press cured at 4200 p.s.i. (29 megapascals) at 175° C. for 20 minutes, and post cured for 16 hours at 140° C. Test specimens were cut from the cured samples and the tensile strength and elongation of the elastomeric specimens were measured according to ASTM D-412. Other test specimens were wrapped in an underwrapping of poly(tetrafluoroethylene) film and an over wrapping of aluminum foil. The wrapped specimens of each composition were placed in separate iron pipes and the sealed pipes were heated to 265° C. for 24 hours. The tensile strength of the cured composition of this invention (i) decreased from the initial value of 1.88 megapascals (MPa) to 0.46 MPa after the heat treatment, a 75.5% loss of tensile strength. The corresponding elongation value decreased from 380% to 205%, a 46.1% loss of elongation. The tensile strength of composition (ii) decreased from the initial value of 1.72 MPa to 0.10 MPa, a 94.2% loss of tensile strength. The corresponding elongation value decreased from 470% to 180%, a 61.7% loss of elongation. This example illustrates the improved reversion resistance of the cured compositions of this invention (i) at 265° C.

EXAMPLE 5

A homogeneous composition consisting of 100 parts of a random siloxane of the formula (IV) wherein R' is $CH_3$—, R is $CF_3CH_2CH_2$—, $R_f$ is —$CF_2CF_2$—, and $p = q = 21$, 10 parts of a trimethylsiloxy-treated fume silica and 2 parts of carbon black was prepared and divided into two equal portions. One portion was thoroughly mixed with 0.5 part of methylbutynol, 1 part of a platinum-containing catalyst having 0.5 percent by weight of platinum and 2.68 parts of the fluorocarbon siloxane of Example 2. The ratio of silicon-bonded hydrogen atoms to silicon-bonded vinyl radicals in the resulting curable composition (iii) was approximately 2. The other portion was thoroughly mixed with 0.5 part of methylbutynol, 1 part of the platinum-containing catalyst having 0.5 percent by weight platinum and 2.82 parts of the known $H(CH_3)_2SiO\{H(CH_3)_2$—$SiO(CF_3CH_2CH_2)SiO\}_mSi(CH_3)_2H$ where $m$ had an average value of approximately 4. The resulting curable composition (iv) had a ratio of silicon-bonded hydrogen atoms to silicon-bonded vinyl radicals of 2. The curable compositions (iii) was press cured for 30 minutes at 165° C. under 27.6 MPa (4000 p.s.i.) pressure. The curable composition (iv) was press cured for 20 minutes at 160° C. under the same pressure.

Test specimens were prepared from the cured compositions and prepared for testing as described in Example 4. The testing conditions and results are shown in Table I.

TABLE I

| Composition | Physical Properties after Indicated Treatment | | | | | | | |
|---|---|---|---|---|---|---|---|---|
| | Original Sample | | After 24 hours at 250° C | | After 24 hours at 275° C | | After 140 hours at 250° C | |
| | T(MPa) | E(%) | T(MPa) | E(%) | T(MPa) | E(%) | T(MPa) | E(%) |
| (iii) | 1.90 | 360 | 1.97 | 150 | 0.63 | 140 | 0.70 | 20 |
| (iv)* | 2.99 | 236 | 3.52 | 267 | 2.00 | 330 | 0 | 0 |
| (v) | 2.35 | 100 | 1.88 | 78 | 1.32 | 83 | — | — |
| (vi)* | 1.50 | 103 | 1.15 | 82 | 1.40 | 128 | 1.55 | 140 |

*For reference purposes only

EXAMPLE 6

A homogeneous composition consisting of 100 parts of an alternating siloxane of the formula (V) wherein R' is $CH_3-$, R is $CF_3CH_2CH_2-$, $R_f$ is $-CF_2CF_2-$, $a$ has a value of 1 and $q$ has an average value of approximately 15, 10 parts of a trimethylsiloxy-treated fume silica, 2 parts of carbon black, 0.1 parts of methylbutynol and 0.5 parts of a platinum-containing catalyst was prepared and divided into two equal portions. One portion was thoroughly mixed with an additional 0.1 parts of methylbutynol, an additional 0.2 parts of a platinum-containing catalyst and 2.60 parts of the curing agent of (iii) to produce curable composition (v). The other portion of the homogeneous composition was mixed with 2.73 parts of the curing agent of (iv) to produce curable composition (vi).

Curable composition (v) was press cured for 25 minutes at 165° C. under 27.5 MPa pressure. Curable composition (vi) was press cured for 25 minutes at 175° C. under 27.6 MPa pressure and then post cured for 16 hours at 155° C. Test specimens were prepared and tested as described in Example 5. Results are shown in Table I.

EXAMPLE 7

A curable composition was prepared in a two-package form. A first package, prepared on a 2-roll rubber compounding mill, consisted of 100 parts of an alternating siloxane of the formula (V) wherein R' is $CH_3-$, R is $CF_3CH_2CH_2-$ $R_f$ is $-CF_2CF_2$, $a$ has a value of 1 and $q$ has an average value of approximately 12; 25 parts of a trimethylsiloxy-treated fume silica, 1.25 part of carbon black, 1.25 part of ZnO and 0.31 parts of a platinum-containing catalyst. A second package, also prepared on a two-roll rubber compounding mill, consisted of 8.3 parts of the siloxane (V) above, 0.44 part of $TiO_2$, a curing agent consisting of 2.28 parts of the fluorocarbon siloxane of Example 2 and 1.71 parts of the fluorocarbon siloxane of Example 3; and 0.02 parts of methylbutynol.

The two packages were mixed and the resulting curable composition was cast in a chase and cured for 1 hour at 150° C. at atmospheric pressure. The curable composition had a ratio of silicon-bonded hydrogen to silicon-bonded vinyl of 0.78, an average of 3.5 silicon-bonded hydrogen atoms per molecule of curing agent and approximately 15 ppm. platinum. Test specimens were prepared from the cured composition and physical properties were measured. Other test specimens were exposed to JP-7 fuel vapor at 5 p.s.i. (34.5 kPa) and 260° C. for 10 days and their physical properties were measured. Physical properties for the cured composition of this example were the following; where the first number of each physical property is for the cured composition and the second number is for the cured composition after it had been exposed to JP-7 fuel vapor as indicated; tensile strength (2.25 MPa/1.07 MPa), elongation (443%/140%), tear strength 8.06 kN/m/8.76 kN/m), durometer (12/35).

This example illustrates the usefulness of the compositions of this invention as an elastomeric material in the presence of hydrocarbon fuel at elevated temperature.

That which is claimed is:

1. A curable composition consisting essentially of a homogeneous mixture of (A) a siloxane polymer or copolymer of the formula

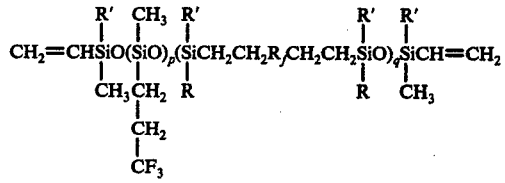

(B) a curing agent of the formula

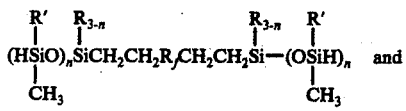

(C) an effective amount of a platinum-containing catalyst; where, in (A) and (B), each R and R' is independently methyl, phenyl, or 3,3,3-trifluoropropyl, each $R_f$ is independently a perfluoroalkylene radical of 2 to 10 carbon atoms, a perfluorocycloalkylene radical, or a perfluoroalkylene radical of 2 to 10 carbon atoms or a perfluorocycloalkylene radical containing one or more —C—O—C— linkages; $p$ has a value of 0 to $2q$ inclusive, so that, when $p = 0$, siloxane (A) is a siloxane polymer, but when $p$ has a value of from greater than 0 to $q$, inclusive, siloxane (A) can be either a random copolymer or an alternating copolymer and when $p$ has a value of from greater than $q$ to $2q$, inclusive, siloxane (A) is only an alternating copolymer having no more than 2 adjacent $CH_3(CF_3CH_2CH_2)SiO$ units, $q$ has an average value of at least 5, each $n$ is independently 1, 2, or 3, there being an average of greater than 2.0 silicon-bonded hydrogen atoms per molecule of (B) and the amount of (B) being such that there is, in said curable composition, from 0.5 to 3.0 silicon-bonded hydrogen atoms for every silicon-bonded vinyl radical.

2. The curable composition of claim 1 which further contains a filler.

3. The curable composition of claim 2 which further contains an inhibitor for the platinum-containing catalyst.

4. The curable composition of claim 3 wherein R' is methyl.

5. The curable composition of claim 4 wherein $R_f$ contains from 2 to 6 carbon atoms.

6. The curable composition of claim 5 wherein $R_f$ is —$CF_2CF_2$—.

7. The curable composition of claim 6 wherein (B) consists essentially of

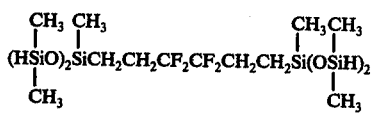

and from 0 to less than 100 mole percent of

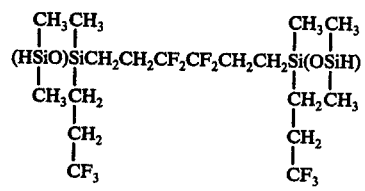

8. The curable composition of claim 6 wherein (B) consists essentially of a mixture of from 40 to 60 mole percent

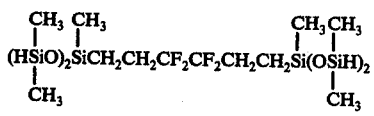

and from 40 to 60 mole percent

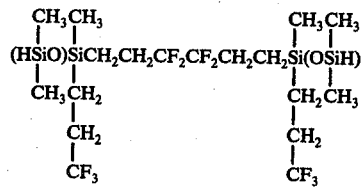

9. The composition of claim 7 wherein the siloxane (A) is a siloxane polymer of the formula

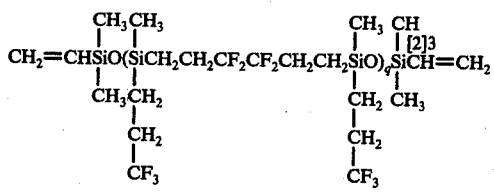

wherein $q$ has a value of at least 5.

10. The composition of claim 7 wherein the siloxane (A) is a random siloxane of the formula

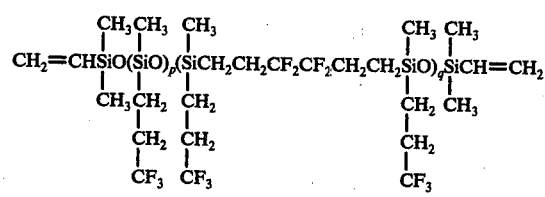

wherein $q$ has a value of at least 5, and $p$ has a value of from greater than zero to $q$, inclusive.

11. The composition of claim 7 wherein the siloxane (A) is an alternating siloxane copolymer of the formula

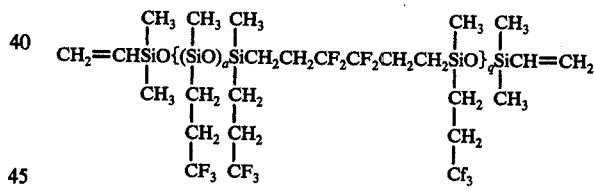

wherein $a$ has an average value of from greater than zero to 2 inclusive, and $q$ has a value of at least 5.

12. The cured composition obtained by heating the curable composition of claim 1.

13. The cured composition obtained by heating the curable composition of claim 1.

14. The cured composition obtained by heating the curable composition of claim 8.

UNITED STATES PATENT AND TRADEMARK OFFICE
CERTIFICATE OF CORRECTION

PATENT NO. : 4,100,136
DATED : July 11, 1978
INVENTOR(S) : Philip L. Carter, Yung K. Kim, & Michael O. Riley It is certified that error appears in the above-identified patent and that said Letters Patent are hereby corrected as shown below:

In Column 8, line 53; "$E^{19}$" should read "$F^{19}$".

In Column 12, line 7; the word reading "indicated;" should read "indicated:".

In Column 14, line 52; the number reading "1" should read "7".

Signed and Sealed this

Thirteenth Day of October 1981

[SEAL]

Attest:

Attesting Officer

GERALD J. MOSSINGHOFF

Commissioner of Patents and Trademarks